United States Patent [19]
Harada et al.

[11] Patent Number: 5,560,366
[45] Date of Patent: Oct. 1, 1996

[54] OSCILLOMETRIC BLOOD PRESSURE MEASURING APPARATUS

[75] Inventors: Chikao Harada; Akihiro Yokozeki, both of Komaki; Toshihiko Ogura, Inuyama, all of Japan

[73] Assignee: Colin Corporation, Aichi-ken, Japan

[21] Appl. No.: 273,929

[22] Filed: Jul. 12, 1994

[30] Foreign Application Priority Data

Nov. 29, 1993 [JP] Japan .................................. 5-298383

[51] Int. Cl.⁶ ................................................ A61B 5/00
[52] U.S. Cl. ........................... 128/681; 128/682; 128/687
[58] Field of Search .................................... 128/672, 677, 128/680–683, 687

[56] References Cited

U.S. PATENT DOCUMENTS

| | | | |
|---|---|---|---|
| 4,699,152 | 10/1987 | Link | 128/681 |
| 4,776,344 | 10/1988 | Shirasaki et al. | 128/681 |
| 4,944,305 | 7/1990 | Takatsu et al. | |
| 4,949,710 | 8/1990 | Dorsett et al. | 128/681 |
| 5,054,494 | 10/1991 | Lazzaro et al. | 128/681 |
| 5,099,853 | 3/1992 | Uemura et al. | 128/681 |
| 5,238,000 | 8/1993 | Niwa | 128/689 |
| 5,368,039 | 11/1994 | Moses | 128/682 |
| 5,423,324 | 6/1995 | Tomita | 128/680 |

FOREIGN PATENT DOCUMENTS

| | | |
|---|---|---|
| 297146 | 1/1989 | European Pat. Off. . |
| 2257529 | 1/1993 | United Kingdom . |

OTHER PUBLICATIONS

Patent Abstracts of Japan, vol. 16, No. 375 (C–0973), Nunome Tomohiro, 12 Aug. 1992.

*Primary Examiner*—Angela D. Sykes
*Assistant Examiner*—Robert L. Nasser, Jr.
*Attorney, Agent, or Firm*—Oliff & Berridge

[57] ABSTRACT

An oscillometric blood pressure measuring apparatus, including an inflatable cuff adapted to be wound around a body portion of a living subject, an oscillometric blood pressure measuring device which supplies a fluid pressure to the cuff to press the body portion of the subject, detects variation of a plurality of pulse amplitudes of a pulse wave which is produced in the cuff in synchronism with heartbeat of the subject while the fluid pressure of the cuff is changed, and determines a blood pressure of the subject based on the variation of the pulse amplitudes, a cuff pulse-wave detecting device which detects a pulse wave which is produced in the cuff when the fluid pressure of the cuff takes a reference pressure value not higher than a mean blood pressure of the subject, and produces a pulse wave signal representative of the detected pulse wave, and a waveform storing device including a waveform memory, for storing a waveform of a pulse wave of the subject by utilizing the pulse wave signal produced by the cuff pulse-wave detecting device.

11 Claims, 7 Drawing Sheets

OSCILLOMETRIC BLOOD PRESSURE MEASURING APPARATUS

BACKGROUND OF THE INVENTION

1. Field of the Invention

The present invention relates to an oscillometric blood pressure measuring apparatus which detects a pulse wave of a living subject and enables a doctor to make a diagnosis based on the waveform of the pulse wave.

2. Related Art Statement

The waveform of a pulse wave produced from an artery of a living body or subject provides useful information reflecting the condition of blood circulation of the subject. There have been proposed various diagnosing apparatus which analyze the waveform of a pulse wave of a subject and make a diagnosis on the circulatory organ of the subject based on the analyzed results.

Generally, the conventional diagnosing apparatus employ (a) an arterial catheter which is invasively inserted into an artery of a subject, and (b) a pressure sensor for directly detecting a pulse wave from inside the artery. Additionally, U.S. Pat. No. 5,238,000 discloses a pressure pulse wave sensor which is pressed on the skin of a subject for indirectly detecting a pressure pulse wave produced from an artery under the skin.

In the first, direct pulse wave detecting technique, a skilled doctor is needed to carry out the insertion of the catheter into the artery, and the arterial invasion due to the catheter insertion gives serious stress to the subject. In the second, indirect pulse wave detecting technique, an exclusive pressure pulse wave sensor is needed, so that the overall apparatus becomes complicated and expensive. Also, it is more or less cumbersome to set the sensor on the skin of the subject.

SUMMARY OF THE INVENTION

It is therefore an object of the present invention to provide an oscillometric blood pressure measuring apparatus which detects a pulse wave of a living subject and enables a doctor to make a diagnosis based on the waveform of the pulse wave, in a non-invasive manner in which an invasive pulse wave detecting device is not used.

The above object has been achieved by the present invention which provides an oscillometric blood pressure measuring apparatus, comprising (a) an inflatable cuff adapted to be wound around a body portion of a living subject; (b) an oscillometric blood pressure measuring device which supplies a fluid pressure to the cuff to press the body portion of the subject, detects variation of a plurality of pulse amplitudes of a pulse wave which is produced in the cuff in synchronism with heartbeat of the subject while the fluid pressure of the cuff is changed, and determines a blood pressure of the subject based on the variation of the pulse amplitudes; (c) a cuff pulse-wave detecting device which detects a pulse wave which is produced in the cuff when the fluid pressure of the cuff takes a reference pressure value not higher than a mean blood pressure of the subject, and produces a pulse wave signal representative of the detected pulse wave; and (d) a waveform storing device including a waveform memory, for storing a waveform of a pulse wave of the subject by utilizing the pulse wave signal produced by the cuff pulse-wave detecting device.

In the oscillometric blood pressure (BP) measuring apparatus constructed as described above, the cuff pulse-wave detecting device detects a pulse wave ("cuff pulse wave") which is produced in the cuff when the fluid pressure of the cuff ("cuff pressure") takes a reference pressure not higher than a mean blood pressure of the subject. Based on the pulse wave signal representative of the cuff pulse wave, the waveform storing device stores a waveform of a pulse wave of the subject in the waveform memory. Since the cuff pulse wave detected as the pressure oscillation produced in the cuff when the cuff pressure takes a reference pressure not higher than the mean blood pressure of the subject, has substantially the same waveform as that of a pulse wave directly or invasively detected as the pressure oscillation produced in an artery of the subject. Therefore, the present apparatus detects a pulse wave of a living subject and enables a doctor to make a diagnosis based on the waveform of the pulse wave, in a non-invasive manner in which an invasive pulse wave detecting device is not used. With the present apparatus, a pulse wave diagnosis can be carried out with ease, at low cost, and without serious stress to the subject due to invasive pulse wave detection.

According to a feature of the present invention, the BP measuring apparatus further comprises an output device which outputs the waveform stored in the waveform memory, so that a doctor can make a diagnosis based on the output waveform. The output device may comprise at least one of (a) a display device which displays the waveform stored in the waveform memory and (b) a recording device which records, on a recording medium, the waveform stored in the waveform memory. Since the output waveform has substantially the same waveform as that of a pulse wave invasively detected from inside an artery of the subject, the doctor can make a correct diagnosis on the subject.

According to another feature of the present invention, the BP measuring apparatus further comprises waveform analyzer means for analyzing the waveform stored in the waveform memory, so that a doctor can make a diagnosis based on the analyzed results of the waveform analyzer means. The waveform analyzer means may operate for analyzing various parameters of the waveform according to various pulse wave diagnosis algorithms known in the art. Since the pulse wave stored in the waveform memory has substantially the same waveform as that of a pulse wave invasively detected from an artery of the subject, the doctor can make a correct diagnosis on the subject based on the analyzed results.

According to yet another feature of the present invention, the cuff pulse-wave detecting device comprises means for detecting the pulse wave which is produced in the cuff when the fluid pressure of the cuff takes the reference pressure value within a pressure range between the mean blood pressure of the subject and a diastolic blood pressure of the subject.

According to a further feature of the present invention, the present apparatus further comprises: a mean blood pressure measuring device which measures the mean blood pressure of the subject; and a cuff pressure holding device which holds the fluid pressure of the cuff at the reference pressure value not higher than the mean blood pressure of the subject measured by the mean blood pressure measuring device, wherein the cuff pulse-wave detecting device detects the pulse wave which is produced in the cuff when the fluid pressure of the cuff is held at the reference pressure value by the cuff pressure holding device. In this case, it is not necessary to remove, from the pulse wave detected from the cuff, detection errors which are introduced thereinto if the pulse wave is detected while the fluid pressure of the cuff is changed.

According to another feature of the present invention, the mean blood pressure measuring device comprises means for measuring the mean blood pressure of the subject while the fluid pressure of the cuff is increased to a prescribed pressure value, and the cuff pressure holding means comprises means for holding the fluid pressure of the cuff at the reference pressure value not higher than the mean blood pressure of the subject while the fluid pressure of the cuff is decreased from the prescribed pressure value. In this case, it is possible to carry out the blood pressure measurement and the pulse wave detection and storing during a single cycle of inflation and deflation of the cuff.

According to another feature of the present invention, the mean blood pressure measuring device comprises means for determining, as the mean blood pressure of the subject, a fluid pressure of the cuff at a time of detection of a pulse having a greatest amplitude of the respective amplitudes of a plurality of pulses of a pulse wave which is produced in the cuff while the fluid pressure of the cuff is changed. Alternatively or additionally, the mean blood pressure measuring device may comprise means for determining, as the mean blood pressure of the subject, a fluid pressure of the cuff at a time when a value of correlation between each pair of successive pulses of a plurality of pulses of a pulse wave which is produced in the cuff while the fluid pressure of the cuff is changed, is changed by a prescribed amount. In these cases, it is possible to measure the mean blood pressure of the subject without again inflating the cuff after deflating the same.

According to another feature of the present invention, the oscillometric blood pressure measuring device comprises: a pressure pulse wave sensor which detects a radial pulse wave produced from a radial artery of the subject; transfer function correcting means for correcting a standard transfer function from a pulse wave produced in an aorta of a standard human being to a pulse wave of the human being detected from the cuff by the cuff pulse-wave detecting device, based on the radial pulse wave of the subject detected by the pressure pulse wave sensor and the pulse wave of the subject detected from the cuff by the cuff pulse-wave detecting device; and calculating means for providing an estimated aortic pulse wave based on the pulse wave of the subject detected from the cuff by the cuff pulse-wave detecting device, according to the corrected transfer function provided by the transfer function correcting means, wherein the waveform storing device stores, in the waveform memory, the waveform of the aortic pulse wave provided by the calculating means. In this case, the BP measuring apparatus provides the reliable and accurate aortic pulse wave, so that a doctor can make a correct diagnosis based on the waveform of the aortic pulse wave.

BRIEF DESCRIPTION OF THE ACCOMPANYING DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
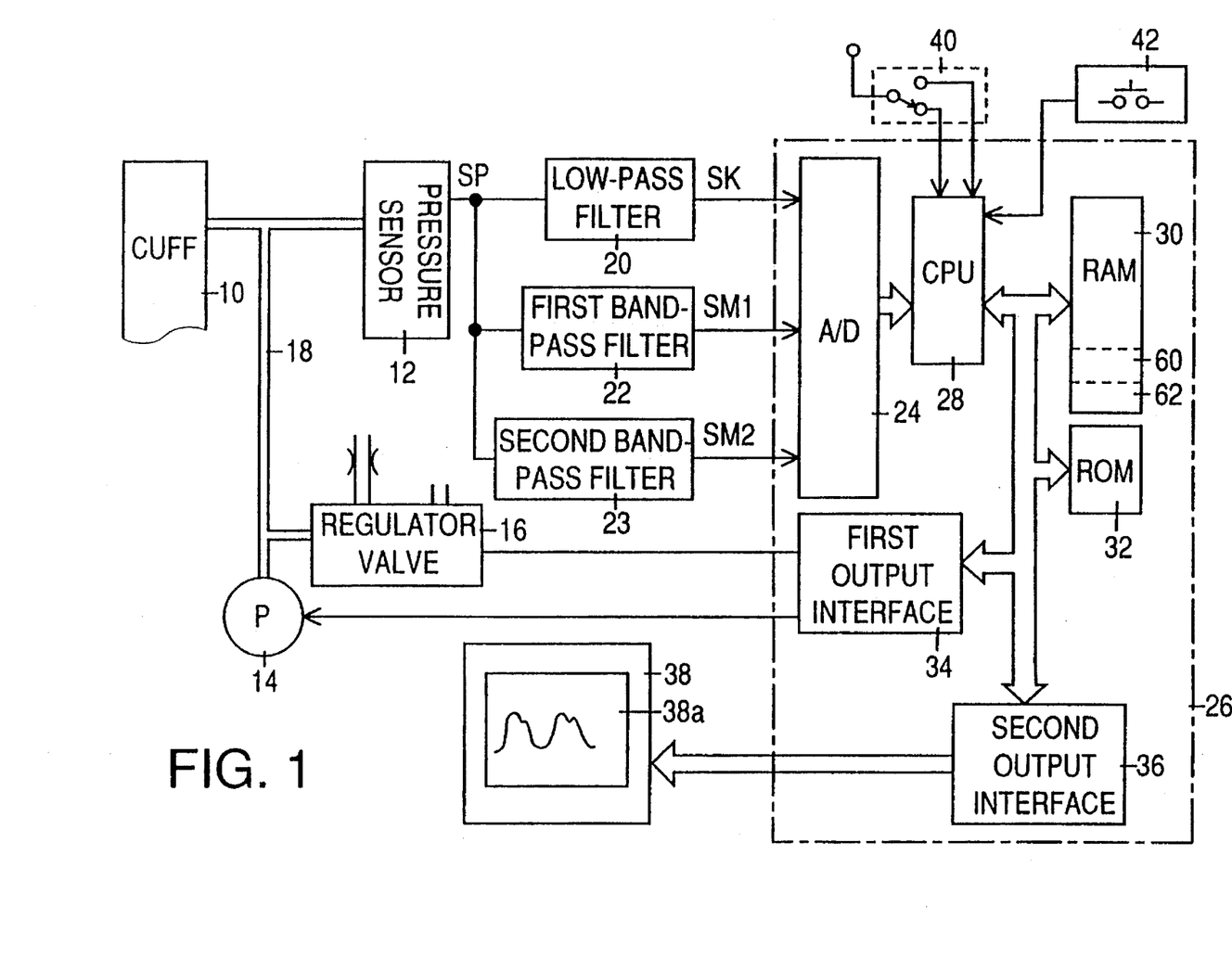
FIG. 1 is a diagrammatic view of the overall construction of an oscillometric blood pressure measuring apparatus embodying the present invention.

Referring first to FIG. 1, there is shown an oscillometric blood pressure (BP) measuring apparatus embodying the present invention. Reference numeral 10 designates an inflatable cuff adapted to be wound around a body portion (e.g., upper arm) of a living subject (e.g., patient) so as to press the upper arm. The inflatable cuff 10 has a bag structure formed of an elastic sheet (e.g., rubber or vinyl sheet). The cuff 10 is connected via piping 18 to a pressure sensor 12, an air pump 14, and an air-deflation regulator valve 16.

The pressure sensor 12 includes, for example, a semiconductor pressure sensing element (not shown) which detects an air pressure in the cuff 10 ("cuff pressure") and supplies a detection signal, SP, representative of the detected cuff pressure, to a low-pass filter 20, a first band-pass filter 22, and a second band-pass filter 23. The low-pass filter 20 permits only a DC (direct current) or static-pressure component of the detection signal SP to pass therethrough, thereby supplying a cuff-pressure signal, SK, representative of the detected static cuff pressure, to an analog to digital (A/D) converter 24.

The first band-pass filter 22 permits only a 1 to 10 Hz frequency AC (alternating current) component of the detection signal SP to pass therethrough, thereby supplying a first pulse wave signal, SM1, representative of a pulse wave of the subject, to the A/D converter 24. The pulse wave is produced in the cuff 10 because of the pulsation of arteries in the upper arm in synchronism with heartbeat of the subject, while the cuff pressure falls within an appropriate pressure range. The pulse wave produced in the cuff 10 is obtained as the AC component of the detection signal SP supplied from the pressure sensor 12.

The second band-pass filter 23 permits only a 0.5 to 20 Hz frequency AC component of the detection signal SP to pass therethrough, thereby supplying a second pulse wave signal, SM2, representative of the pulse wave of the subject, to the A/D converter 24. The first band-pass filter 22 has a narrow specific frequency range (e.g., 1 to 10 Hz) for obtaining, from the detection signal SP, successive pulse amplitudes free from artifact noise possibly introduced thereinto because of physical motion of the subject. On the other hand, the second band-pass filter 23 has a comparatively wide specific frequency range (e.g., 0.5 to 20 Hz) for obtaining, from the same signal SP, a pulse wave having a waveform similar to that of a pulse wave which is directly or invasively obtained from inside an artery of the subject. The A/D converter 24 has a time division multiplexer for time sharing of the three analog signals SK, SM1, SM2, and concurrently converts those analog signals to respective digital signals.

The present BP measuring apparatus also has an arithmetic control device 26 which is essentially constituted by a microcomputer including a central processing unit (CPU) 28, a random access memory (RAM) 30, a read only memory (ROM) 32, a first output interface 34, and a second output interface 36. The CPU 28 receives the three digital signals SK, SM1, SM2 from the A/D converter 24, and processes those signals by utilizing the temporary-storage function of the RAM 30 and the various control programs pre-stored in the ROM 32, so that the CPU 28 controls the operations of the air pump 14 and the air-deflation regulator valve 16 through the first output interface 34 and controls an output device 38 through the second output interface 36. The output device 38 includes a printer which records, with an ink and on a recording sheet, the measured blood pressure (BP) values and detected pulse wave of the subject. The output device 38 also includes an image display 38a constituted by a number of light emitting elements (e.g., light emitting diodes). The image display 38a displays the measured blood pressure values and the waveform of detected pulse wave.

A mode switch 40 is operable for selecting one of a BP measurement mode and a pulse wave diagnosis mode. The mode switch 40 selectively supplies one of a first signal indicative of the BP measurement mode and a second signal indicative of the pulse wave diagnosis mode, to the CPU 28. An ON/OFF switch 42 is operable for starting and stopping the present BP measuring apparatus, and alternatively supplies a START signal and a STOP signal to the CPU 28 upon operation thereof.

Figure 2:
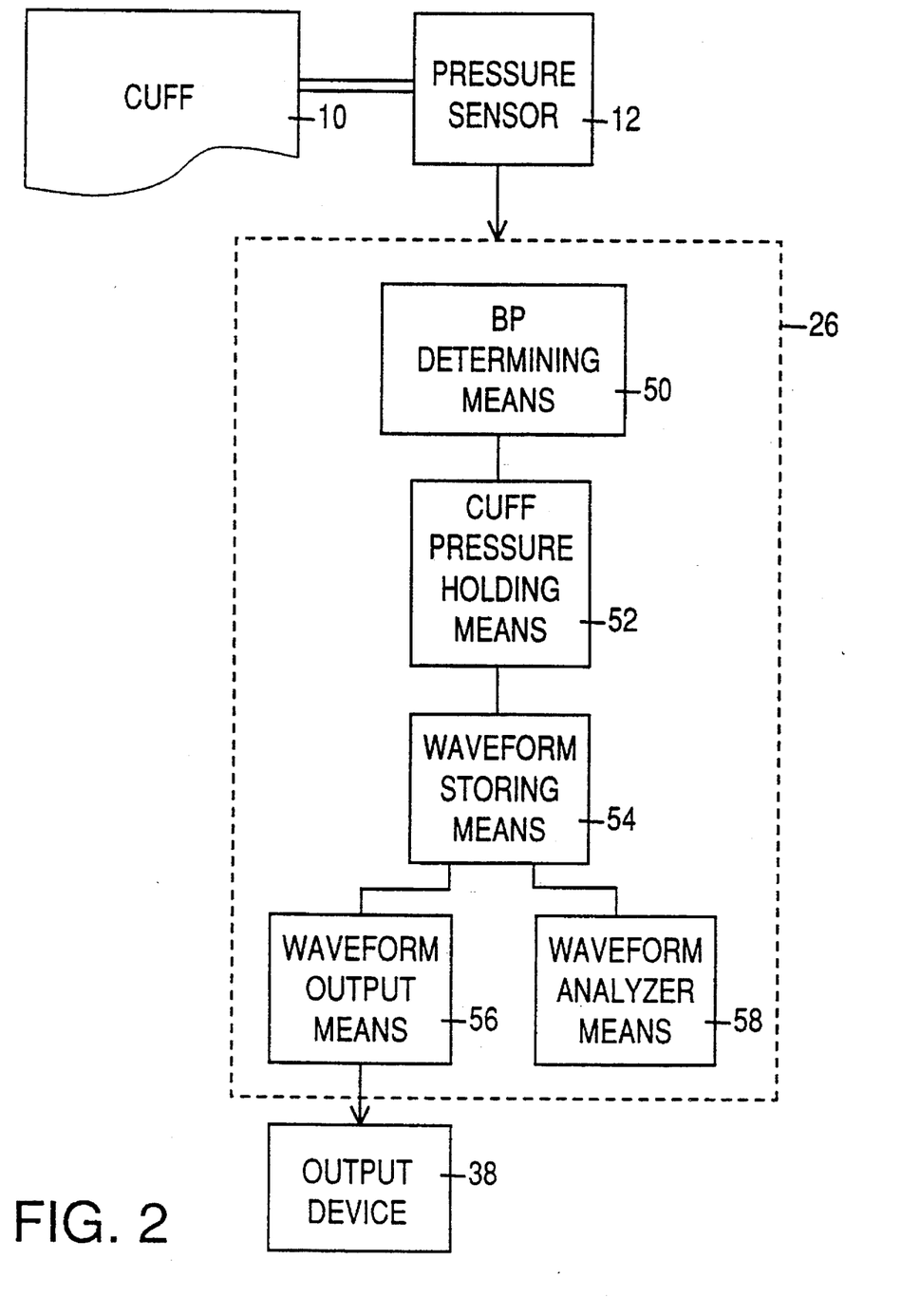
FIG. 2 is a diagrammatic view of the various functions of an arithmetic control device 26 of the apparatus of FIG. 1.

Referring to FIG. 2, there are shown various functions of the control device 26. First, the pressure sensor 12 detects a pulse wave which is produced in the cuff 10 wound around the upper arm of the subject in synchronism with heartbeat of the subject while the cuff pressure is changed. The control device 26 has a BP determining function or means 50 for determining a mean BP value of the subject; a cuff pressure holding function or means 52 for holding the cuff pressure at a reference pressure value not higher than the mean BP value of the subject; a waveform storing function or means 54 for storing a waveform of a pulse wave of the subject by utilizing a pulse wave which is produced in the cuff 10 when the cuff pressure is held at the reference pressure value not higher than the mean BP value of the subject; an output function or means 56 for operating the output device 38 to output the stored waveform so that a doctor can make a diagnosis based on the output waveform; and a waveform analyzing function or means 58 for analyzing the stored waveform so that a doctor can make a diagnosis based on the analyzed results.

Hereinafter there will be described the operation of the oscillometric BP measuring apparatus constructed as described above, by reference to the flow chart of FIG. 3.

Figure 3:
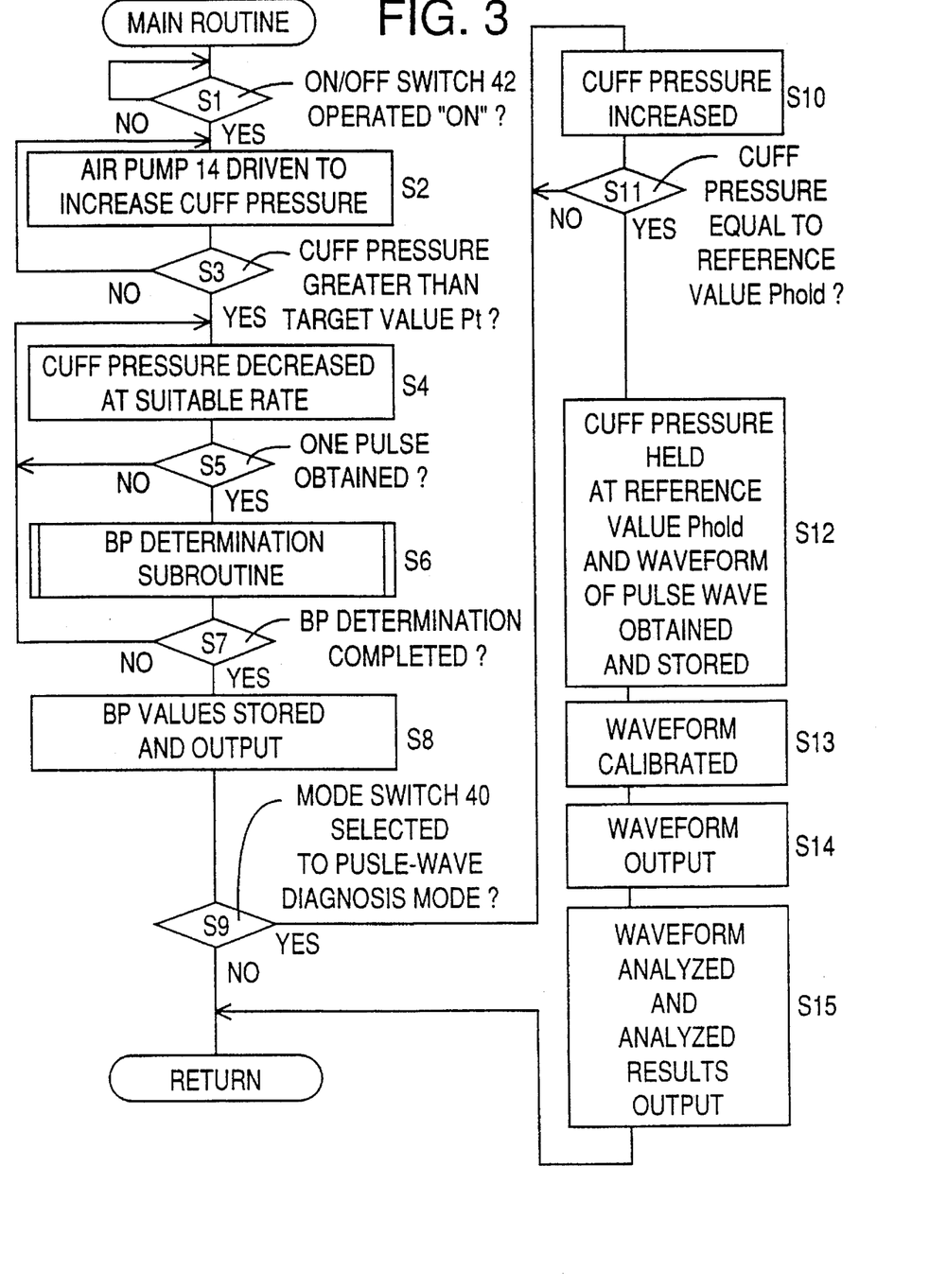
FIG. 3 is a flow chart representing a control program according to which the apparatus of FIG. 1 operates.

Initially, at Step S1, the CPU 28 of the control device 26 judges whether the ON/OFF switch 42 has been operated for starting the operation of the present apparatus, based on the START or STOP signal supplied from the switch 42. If a negative judgment is made at Step S1, the CPU 28 waits for receiving the START signal from the switch 42. Meanwhile, if a positive judgment is made at Step S1, the control of the CPU 28 proceeds with Step S2 to operate the air pump 14 so as to supply a pressurized air to the inflatable cuff 10 and thereby quickly increase the air pressure in the cuff 10, i.e., cuff pressure.

Step S2 is followed by Step S3 to judge whether the cuff pressure has reached a prescribed target pressure value, Pt, (e.g., 180 mmHg) higher than a systolic blood pressure of the subject. If a negative judgment is made at Step S3, the CPU 28 repeats Steps S2 and S3. Meanwhile, if a positive judgment is made at Step S3, the control of the CPU 28 proceeds with Step S4 to change the degree of opening of the air-deflation regulator valve 16 so as to slowly deflate the cuff 10. This slow cuff deflation is carried out at a rate of 2 to 3 mmHg/sec, for example, that is suitable for a BP measurement. Step S4 is followed by Step S5 to judge whether the CPU 28 has received a span of signal SM1 corresponding to a pulse having an amplitude, i.e., corresponding to a heartbeat of the subject. If a negative judgment is made at Step S5, the CPU 28 repeats Steps S4 and S5.

Meanwhile, if a positive judgment is made at Step S5, the control of the CPU 28 proceeds with Step S6 to operate according to a known oscillometric BP determination algorithm, i.e., determine the BP values of the subject. Step S6 is followed by Step S7 to judge whether the BP determination routine at Step S6 has been completed. While the cuff pressure is slowly decreased, the respective amplitudes of successive pulses of the pulse wave first increase and then decrease. The amplitude of one pulse ("pulse amplitude") is obtained by subtracting the lower-peak magnitude of the one-pulse signal SM1 from the upper-peak magnitude of the same. In the known oscillometric BP measurement algorithm, a cuff pressure at the time when the pulse amplitudes significantly largely increase is determined as a systolic BP value, Psys, of the subject; a cuff pressure at the time of detection of the greatest pulse amplitude is determined as a mean BP value, Pmean; and a cuff pressure at the time when the pulse amplitudes significantly largely decrease is determined as a diastolic BP value, Pdia.

If a negative judgment is made at Step S7, the CPU 28 repeats Steps S4 through S7. Meanwhile, if a positive judgment is made at Step S7, the control of the CPU 28 proceeds with Step S8 to store the three BP values Psys, Pmean, Pdia in a BP data memory area 60 provided in the RAM 30, and display those BP values in digits on the image display 38a. Furthermore, the CPU 28 fully opens the air-deflation regulator valve 16 so as to quickly deflate the cuff 10, i.e., quickly decrease the cuff pressure and thereby release the subject's upper arm from the cuff pressure.

Step S8 is followed by Step S9 to judge whether the pulse wave diagnosis mode has been selected, based on the mode signal supplied from the mode switch 40. If a negative judgment is made at Step S9, that is, if the present apparatus is selected to the BP measurement mode, the current control cycle is ended, and the control of the CPU 28 returns to Step S1 and the following steps.

On the other hand, if a positive judgment is made at Step S9, that is, if the present apparatus is selected to the pulse wave diagnosis mode, the control of the CPU 28 goes to Step S10 to close the air-deflation regulator valve 16 and operate the air pump 14 so as to supply a pressurized air to the cuff 10 and thereby increase the cuff pressure at the same rate as that employed at Step S2. Step S10 is followed by Step S11 to judge whether the cuff pressure has reached a reference pressure value, Phold, not higher than the mean BP value Pmean stored in the BP data memory area 60 of the RAM 30. For example, the reference pressure Phold is selected at a value falling within a pressure range between the mean and diastolic BP values Pmean, Pdia, more preferably at a value equal to a cuff pressure at the time of detection of a pulse immediately before the pulse amplitudes largely decrease, that is, pulse preceding a pulse corresponding to the cuff pressure determined as the diastolic BP value Pdia. If a negative judgment is made at Step S11, the CPU 28 repeats Steps S10 and S11. On the other hand, if a positive judgment is made at Step S11, the control of the CPU 28 goes to Step S12.

At Step S12, the CPU 28 stops the operation of the air pump 14 so as to hold the cuff pressure at the reference pressure value Phold, reads in at least one span of signal SM2 corresponding to at least one pulse of the cuff pulse wave, i.e., corresponding to at least one heartbeat of the subject, and stores waveform data representative of the waveform of the read-in pulse wave signal SM2 in a waveform memory area 62 of the RAM 30. Additionally, the CPU 28 opens the air-deflation regular valve 16 so as to quickly decrease the cuff pressure and thereby release the subject's upper arm from the cuff pressure. Step S12 is followed by Step S13 to calibrate the stored waveform with respect to blood pressure, on the assumption that the upper-peak magnitude of the waveform corresponds to the systolic BP value Psys and the lower-peak magnitude of the same corresponds to the diastolic BP value Pdia. The calibrated waveform represents instantaneous blood pressure values of the patient. Subsequently, at Step S14, the CPU 28 operates the output device 38 to display the calibrated waveform on the image display 38a and record the same on a recording sheet, so that a doctor or a heart specialist can make a diagnosis based on the output waveform.

Step S14 is followed by Step S15 to analyze various parameters or characteristics of the waveform stored in the waveform memory area 62 at Step S12 and then calibrated at Step S13. That is, the CPU 28 quantifies the characteristics of the shape or profile of the waveform, according to known pulse wave diagnosis algorithms pre-stored in the ROM 32, and outputs the quantified values through the output device 38, so that a heart specialist can make a diagnosis based on the analyzed results. For example, the CPU 28 calculates a maximum differential or slope, $(dp/dt)_{max}$, of an increasing portion of one-pulse waveform. The parameter $(dp/dt)_{max}$ relates to the strength of cardiac muscle and it is proportional to the cardiac output.

In the present embodiment, Step S6 corresponds to the BP determining means 50 for determining the mean BP value Pmean of the subject; Step S11 corresponds to the cuff pressure holding means 52 for holding the cuff pressure at the reference pressure value Phold not higher than the mean BP value Pmean; the waveform memory area 62 of the RAM 30 corresponds to the waveform storing means 54 for storing the waveform of a pulse wave which is detected when the cuff pressure is held at the reference value Phold; Step S14 corresponds to the output means 56 for operating the output device 38 to output the stored waveform so that a doctor or a heart specialist can make a diagnosis based on the output waveform.

Additionally, in the present embodiment, Step S15 corresponds to the waveform analyzing means 58 for analyzing the waveform stored in the waveform memory area 62 so that a doctor can make a diagnosis based on the analyzed results, for example, a heart specialist can diagnose on the condition of the circulatory organ of the subject based on the analyzed parameter $(dp/dt)_{max}$ and/or other analyzed parameters of the waveform.

Thus, the present oscillometric BP measuring apparatus is capable of providing a reliable and accurate pulse wave of a living subject and enabling a doctor to make a diagnosis based on the waveform of the pulse wave, in a non-invasive manner in which an invasive pulse wave detecting device using an arterial catheter is not needed. With this apparatus, a pulse wave diagnosis can be made with ease and safety and at low cost.

Since in the present embodiment the waveform of pulse wave is obtained while the cuff pressure is held at the reference value Phold, it is not necessary to remove, from the waveform, detection errors introduced thereinto in the case of obtaining the cuff pulse wave while the cuff pressure is continuously changed.

Figure 5:
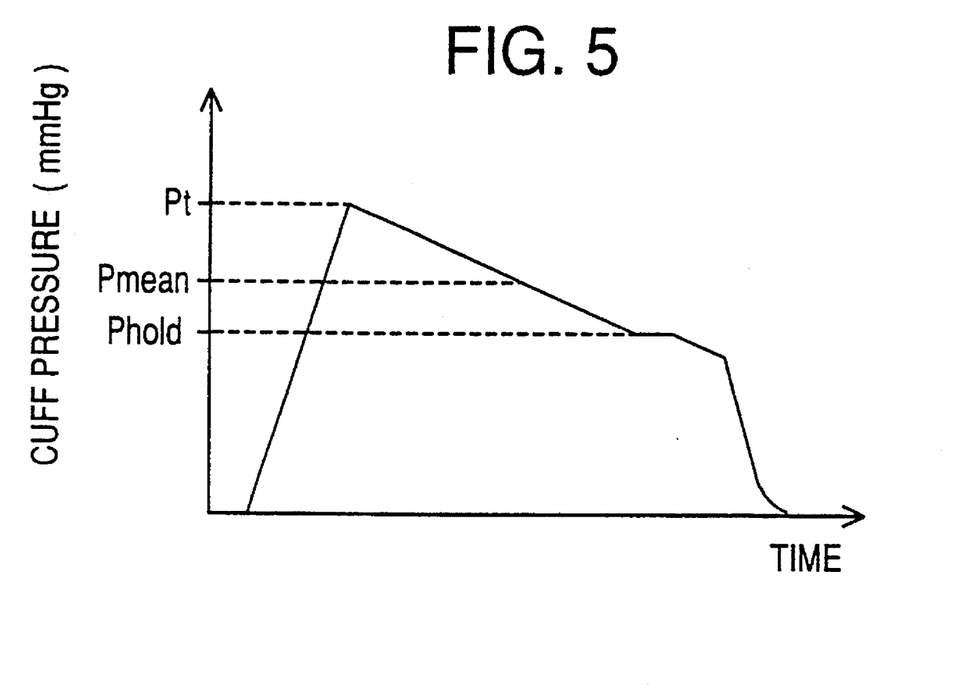
FIG. 5 is a time chart representing the change of cuff pressure while the second embodiment operates according to the flow chart of FIG. 4.
Figure 6:
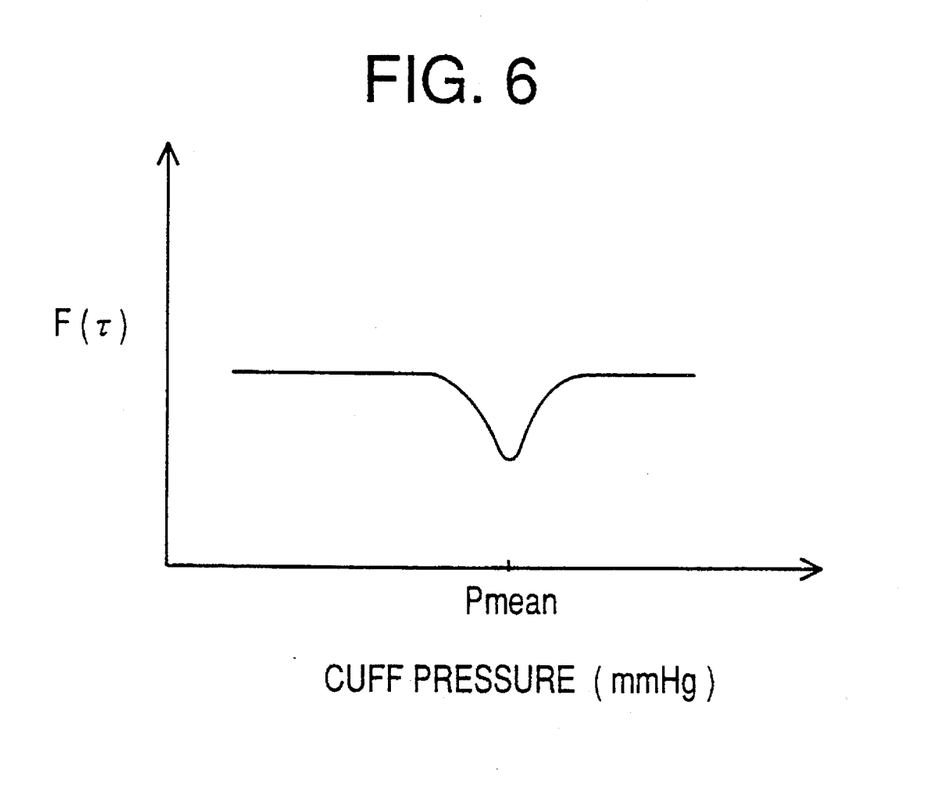
FIG. 6 is a graph showing the change of correlation values which may be utilized in determining a mean blood pressure of a subject in the first and second embodiments of the invention.

There will be described the second embodiment of the present invention by reference to FIGS. 4 through 6. The second embodiment has the same hardware construction as that of the first embodiment of FIG. 1, and operates according to the control program represented by the flow chart of FIG. 4 in place of FIG. 3 for the first embodiment. The same reference numerals and symbols as used for the first embodiment shown in FIGS. 1 and 3 are used for designating the corresponding parts or steps for the second embodiment, and the description of those elements are omitted.

In the second embodiment, if a negative judgment is made at Step S3, the control of the CPU 28 goes to Step S16 to judge whether the CPU 28 has read in a pulse having the greatest amplitude of all the pulses obtained during the cuff pressure inflation effected at Steps S2 and S3. During the cuff pressure inflation effected at Steps S2 and S3, the respective amplitudes of the detected pulses first increase and then decrease. Therefore, the pulse having the greatest amplitude of all the pulses obtained is read in when the respective amplitudes of the detected pulses start decreasing. If a negative judgment is made at Step S16, the CPU 28 repeats Steps S2, S3, and S16. Meanwhile, if a positive judgment is made at Step S16, the control of the CPU 28 proceeds with Step S17 to store, in the BP data memory area 60, a cuff pressure at the time of detection of the pulse having the greatest amplitude, as a mean BP value, Pmean, of the subject, and additionally determine a value not higher than the mean BP value Pmean, for example, value lower by 20 mmHg than the value Pmean, as a reference pressure value, Phold. Step S17 is followed by Step S2.

During the slow cuff deflation at Steps S4 through S7, if a negative judgment is made at Step S5 or S7, the control of the CPU 28 goes to Step S18 to judge whether the cuff pressure has reached the reference value Phold. If a positive judgment is made at Step S18, the control proceeds with Step S19 to close the air-deflation regulator valve 16, hold the cuff pressure at the reference value Phold for a short time, read in the pulse wave signal SM2, and store the waveform of signal SM2 in the waveform memory area 62. Step S19 is followed by Step S4 to continue the slow cuff deflation. FIG. 5 is a time chart representing the change of the cuff pressure during the above-described steps.

In the second embodiment, the oscillometric BP measuring apparatus advantageously obtains the BP values and BP waveform of the subject during a one-time inflation and deflation of the cuff 10.

Figure 4:
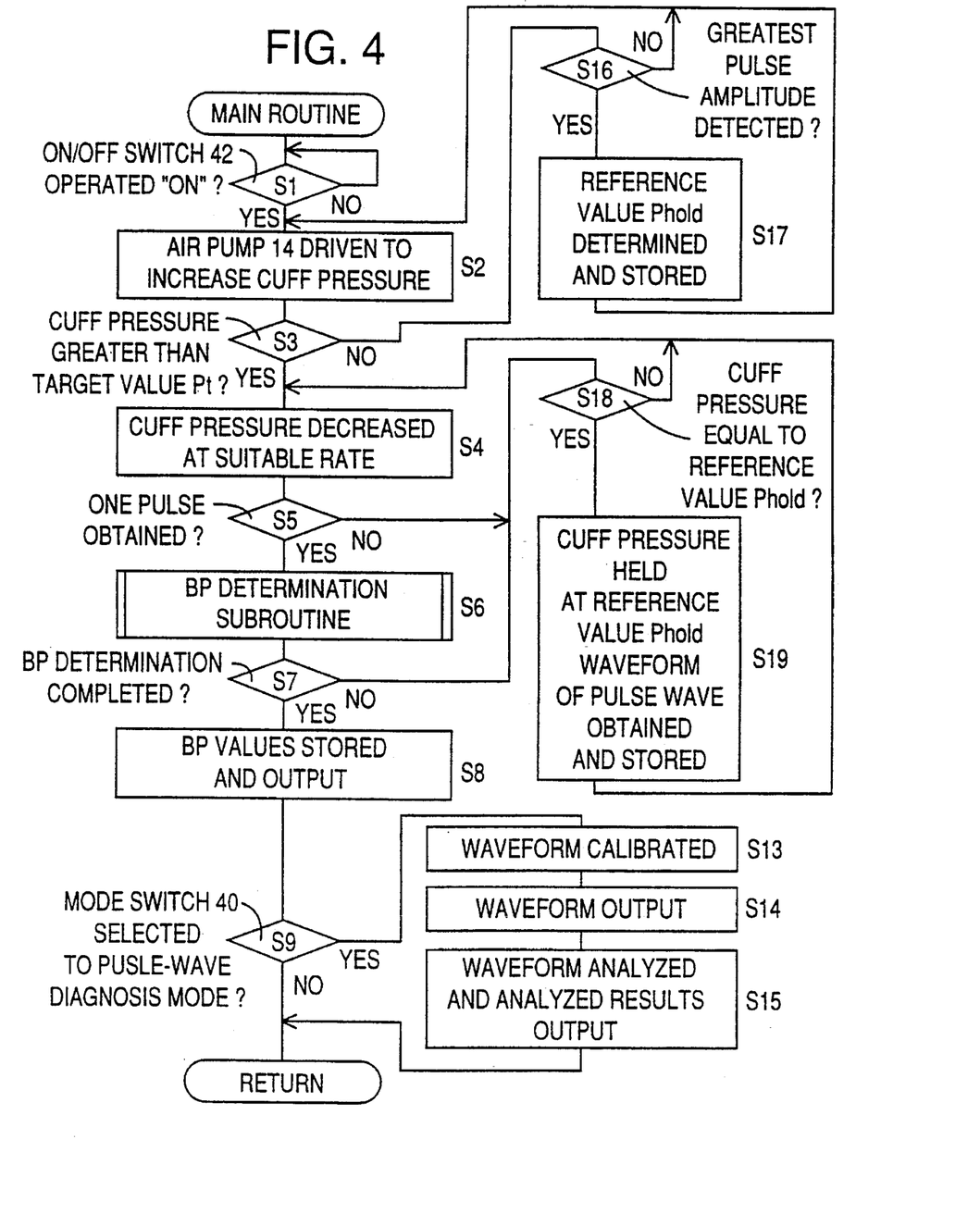
FIG. 4 is a flow chart corresponding to FIG. 3, representing a control program according to which the second embodiment of the invention operates.

At Step S6 of FIG. 3 for the first embodiment and at Step S16 of FIG. 4 for the second embodiment, the mean BP value Pmean of the subject is determined by finding a pulse having the greatest amplitude from the successive pulses of the pulse wave produced in the cuff 10 during the deflation or inflation of the cuff 10. However, at these steps, the mean BP value Pmean of the subject may be determined by other methods. For example, it is possible to determine, as the mean BP value Pmean, a cuff pressure at the time when a value of correlation between each pair of successive pulses out of the individual pulses of the pulse wave produced in the cuff 10 while the cuff pressure is changed, is lowered by more than a prescribed magnitude or amount. The correlation value may be defined by a correction function, $F(\tau)$, expressed by the following equation (1):

$$F(\tau) = \int_{t=0}^{t=\tau} f(t) \cdot f(t-\tau) dt \tag{1}$$

where t is a current time;

$\tau$ is a time retrospectively measured from the current time t;

f(t) is an instantaneous magnitude of first pulse wave signal SM1.

The time $\tau$ is selected at the period of the pulse wave, i.e., time difference between the respective upper (or lower) peaks of two successive pulses of the pulse wave. If the correction value $F(\tau)$ falls by more than a prescribed amount, as shown in FIG. 6, a cuff pressure at the time of detection of that fall is determined as the mean BP value Pmean. The waveform of pulse wave produced in the cuff 10 at the cuff pressure lower than the mean BP value Pmean is different from that at the cuff pressure higher than the mean value Pmean. Therefore, each of the pulses detected at the cuff pressure lower than the mean value Pmean exhibits a high correlation value with respect to the other similar pulses but exhibits a low correlation value with respect to the pulses detected at the cuff pressure higher than the mean value Pmean, and vice versa.

Figure 7:
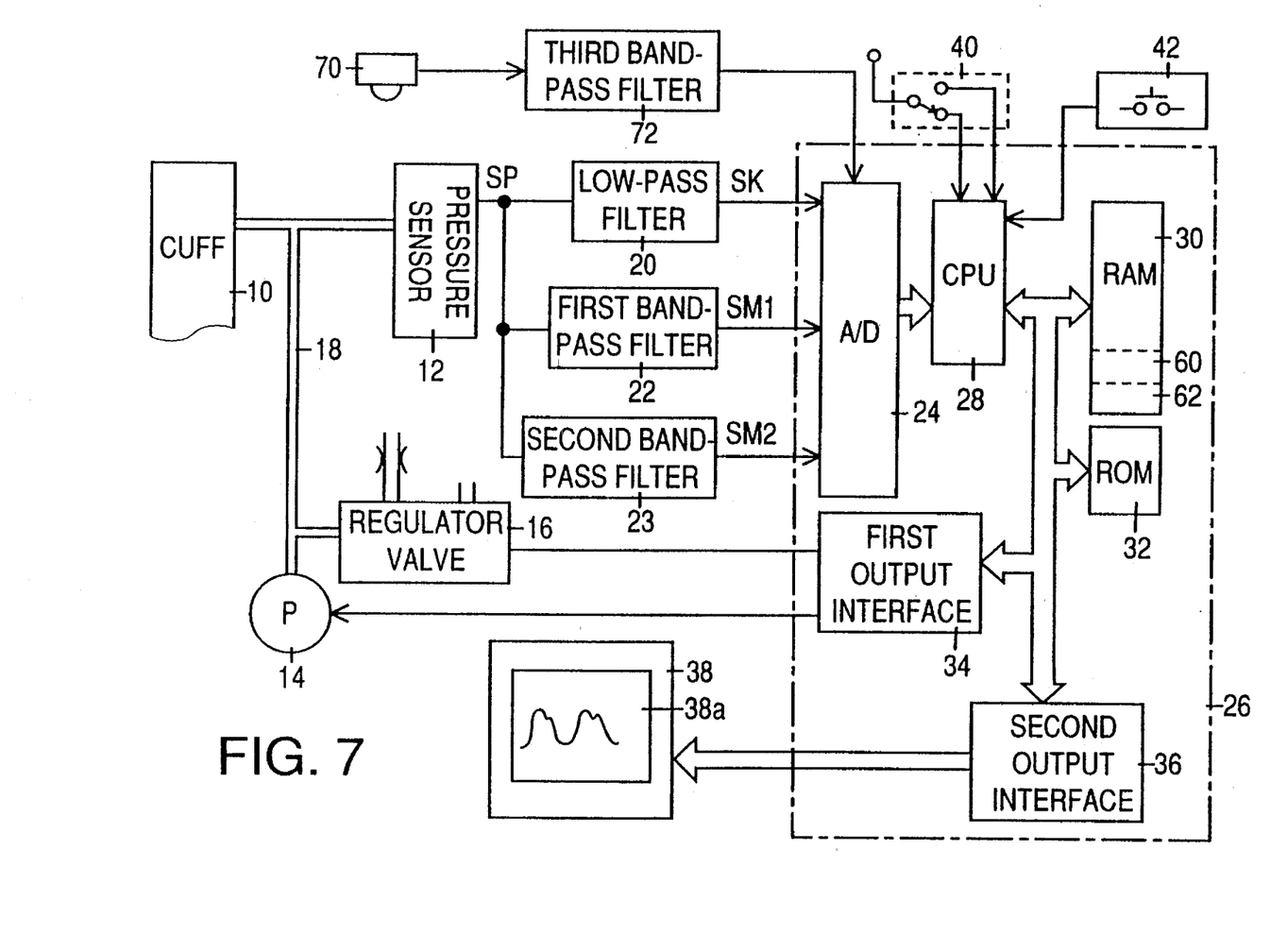
FIG. 7 is a diagrammatic view corresponding to FIG. 1, showing the overall construction of an oscillometric blood pressure measuring apparatus as the third embodiment of the invention.

Referring next to FIG. 7, there is shown the third embodiment of the present invention. The third embodiment relates to an oscillometric BP measuring apparatus like the first and second embodiments, and has a hardware construction similar to that of the apparatus of FIG. 1 wherein, however, the former is different from the latter in that the former additionally includes a pressure pulse wave sensor 70 and a third band-pass filter 72 to which the sensor 70 is connected. The pressure pulse wave sensor 70 has a press surface in which a plurality of pressure sensing elements (not shown) are provided, and the sensor 70 is set on the skin of a wrist or an ankle of the subject in such a way that the press surface of the sensor 70 is pressed against a radial artery or a pedal dorsal artery under the skin so as to detect a pressure pulse wave propagated from the artery to the pressure sensing elements in synchronism with heartbeat of the subject. The third band-pass filter 72 receives the output signal of the sensor 70, and permits only a pressure pulse wave component of the sensor signal to pass therethrough, thereby supplying a pressure pulse wave signal to the A/D converter 24.

Figure 8:
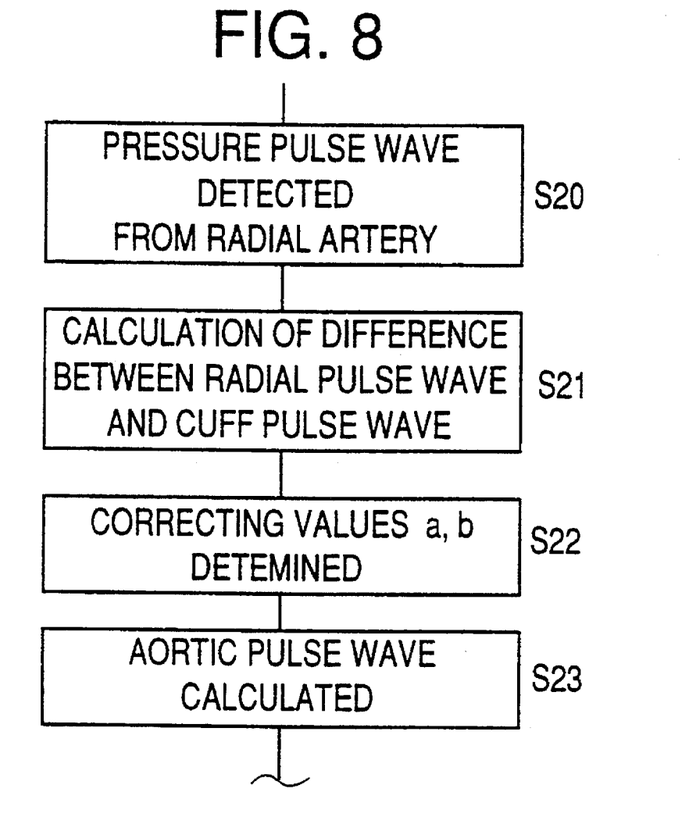
FIG. 8 is a flow chart representing some steps of a control program according to which the apparatus of FIG. 7 operates.

The present apparatus may operate according to the flow chart of FIG. 3 for the first embodiment or the flow chart of FIG. 4 for the second embodiment each of which, however, is modified by adding, after Step S12 of FIG. 3 or Step S19 of FIG. 4, Steps S20 through S23 shown in FIG. 8. At Step S12 or at Step S19, the waveform of pulse wave detected from the cuff 10 (i.e., second pulse wave signal SM2) is stored in the waveform memory area 62 of the RAM 30. In the third embodiment, an aortic pulse wave is estimated by calculation based on the cuff pulse wave (i.e., signal SM2) obtained at Step S12 or Step S19, and the waveform of estimated aortic pulse wave is stored in a waveform memory area 62 of a RAM 30, so that the aortic pulse wave is output by an output device 38 or analyzed by a waveform analyzer means 58.

At Step S20 of FIG. 8, a CPU 28 reads in the signal supplied from the pressure pulse wave sensor 70, that is, the waveform of pressure pulse wave detected from a single superficial artery (e.g., radial artery) of the subject. Step S20 is followed by Step S21 to calculate the difference between the cuff pulse wave detected from a cuff 10 wound around an upper arm of the subject, obtained at Step S12 or Step S19, and the radial pulse wave detected from the radial artery of the subject, obtained at Step S20. The difference between the two sorts of pulse waves may be defined as the area enveloped by a one-pulse signal SM2 and a corresponding one-pulse signal of the sensor 70.

Figure 9:
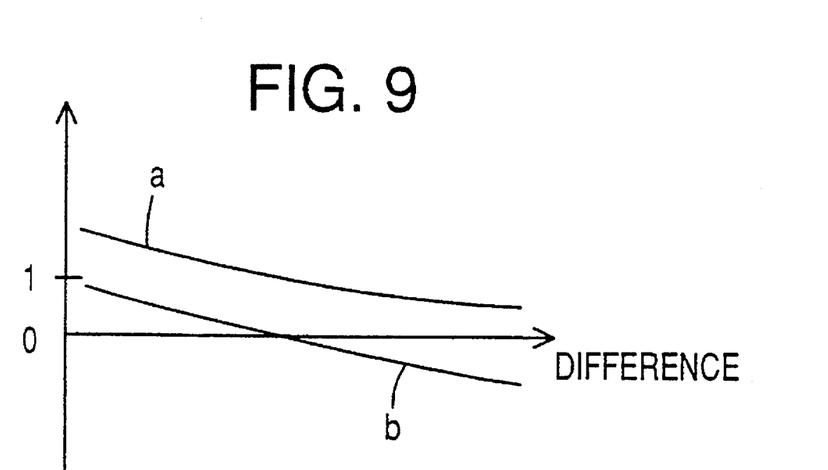
FIG. 9 is a graph showing the relationships between the transfer function correcting values a, b and the difference of the pulse wave detected from a cuff 10 and the radial pulse wave detected from a radial artery of a subject, the relationships being employed by the apparatus of FIG. 7.

Step S21 is followed by Step S22 to determine two correcting values, a and b, of the following expression (2), based on the pulse-wave difference obtained at Step S21, according to predetermined relationships between the values a, b and the pulse-wave difference as shown in FIG. 9. These relationships are, e.g., function equations pre-stored in a ROM 32. The values a and b are small values which can vary depending upon the condition of arteries of the subject.

$$Md(t)=Mk(t)\cdot 1/(aT+b) \tag{2}$$

where T is a standard transfer function from a pulse wave, Md(t), produced in an aorta of a standard human being to a pulse wave, Mk(t), of the human being detected from the cuff 10 wound around the upper arm of the human being.

The transfer function T is pre-determined by experiments. The aorta directly receives the blood flow output from the left ventricle of the heart of the subject. The aortic pulse wave Md(t) is propagated to the cuff 10 wound around the upper arm of the subject and there detected as the cuff pulse wave Mk(t).

Step S22 is followed by Step S23 to estimate or calculate an aortic pulse wave Md(t) of the subject (e.g., one pulse), based on the cuff pulse wave Mk(t) (e.g., one pulse) stored in the waveform memory area 62 at Step S12 or Step S19, according to the above expression (2), and store the obtained waveform of aortic pulse wave Md(t) in the waveform memory area 62 in association with the waveform of cuff pulse wave Mk(t). After the waveform of aortic pulse wave Md(t) is calibrated at S13, the calibrated waveform is output by the output device 38 at Step S14 and is subjected to the pulse wave analysis at Step S15.

In the third embodiment, the aortic pulse wave Md(t) of the subject is obtained by calculation based on the cuff pulse wave Mk(t) of the same. The waveform of aortic pulse wave Md(t) is output and the automatic analysis is carried out based on the waveform Md(t). Therefore, the output waveform and analyzed results become more accurate and reliable, which contributes to improving the doctor's diagnosis relying on the output waveform and/or analyzed results.

While the present invention has been described in its preferred embodiments, the present invention may otherwise be embodied.

For example, while in the illustrated embodiments each blood pressure measurement is carried out with or without a waveform detection and storing, in response to an "ON" operation of the ON/OFF switch 42, it is possible to adapt the BP measuring apparatus to repeatedly carry out a blood pressure measurement with or without a waveform detection and storing at regular intervals of time. In this case, the blood pressure values and/or the waveform and analyzed results may be stored for each of the periodic operations, so that a doctor can utilize the stored data for obtaining not only one-day or 24-hour variation of the blood pressure values and pulse rates but also one-day variation of the analyzed waveform parameters.

In the illustrated embodiments, it is possible to insert, after Step S13, an additional step where the CPU 28 determines a different sort of mean BP value, $Pmean^s$, of the subject by integrating the cuff or aortic pulse wave calibrated at Step S13 (specifically, a cuff pressure corresponding to the gravity center of the integration, i.e., area of the cuff or aortic pulse wave is determined as the mean value $Pmean^s$), and evaluates the reliability of oscillometric blood pressure measurement carried out at Step S6, by comparing the thus obtained mean value $Pmean^s$ and the mean value Pmean obtained by the oscillometric blood pressure measurement at Step S6.

Although in the illustrated embodiments the CPU 28 analyzes the waveform of cuff or aortic pulse wave at Step S15, it is possible that the output device 38 further have the function of recording the waveform stored in the waveform memory area 62, in a recording medium such as a floppy disk, so that a doctor can remove the disk from the output device 38 and insert it into an external waveform analyzer device capable of processing the waveform at a higher speed and/or according to other pulse wave diagnosis algorithms.

While in the illustrated embodiments the CPU 28 reads in, at Step S12 or Step S19, the waveform of pulse wave detected when the cuff pressure is held at the reference value Phold not higher than the mean BP value Pmean of the subject, it is possible to adapt the apparatus such that the CPU 28 reads in the waveform of pulse wave detected while the cuff pressure is continuously changed over a pressure range not higher than the mean BP value Pmean. In this case, it is desirable to employ a data correcting device which removes, from the detected waveform, detection errors introduced thereinto because of the continuous change of the cuff pressure.

The reference pressure value Phold may otherwise be selected at a value lower than the diastolic BP value Pdia. In this case, too, a more accurate waveform of pulse wave can be obtained than that obtained when the cuff pressure is held at a value higher than the mean BP value Pmean.

It is to be understood that the present invention may be embodied with other changes, improvements, and modifications that may occur to those skilled in the art without departing from the spirit and scope of the invention defined in the appended claims.

What is claimed is:

1. An oscillometric blood pressure measuring apparatus, comprising:

an inflatable cuff adapted to be wound around a body portion of a living subject;

an oscillometric blood pressure measuring device which supplies a fluid pressure to said cuff to press said body portion of said subject, detects variation of a plurality of pulse amplitudes of a pulse wave which is produced in said cuff in synchronism with a heartbeat of said subject while said fluid pressure of said cuff is changed, and determines a mean blood pressure of said subject based on said variation of said pulse amplitudes;

a cuff pulse-wave detecting device which determines, based on the determined mean blood pressure of said subject, a reference pressure value of said fluid pressure of said cuff such that the determined reference pressure value is not higher than said determined mean blood pressure, holds said fluid pressure of said cuff at the determined reference pressure value, detects a pulse wave which is produced in said cuff when said fluid pressure of said cuff is held at said determined reference pressure value, and produces a pulse wave signal representative of the detected pulse wave; and a waveform storing device including a waveform memory, for storing a waveform of a pulse wave of said subject by utilizing said pulse wave signal produced by said cuff pulse-wave detecting device.

2. An apparatus according to claim 1, further comprising an output device which outputs said waveform stored in said waveform memory, so that a doctor can make a diagnosis based on the output waveform.

3. An apparatus according to claim 2, wherein said output device comprises at least one of (a) a display device which displays said waveform stored in said waveform memory and (b) a recording device which records, on a recording medium, said waveform stored in said waveform memory.

4. An apparatus according to claim 1, further comprising waveform analyzer means for analyzing said waveform stored in said waveform memory, so that a doctor can make a diagnosis based on the analyzed results of said waveform analyzer means.

5. An apparatus according to claim 1, wherein said cuff pulse-wave detecting device comprises means for detecting said pulse wave which is produced in said cuff when said fluid pressure is at said reference pressure, which is in pressure range between said mean blood pressure of said subject and a diastolic blood pressure of the subject.

6. An apparatus according to claim 1, wherein said oscillometric blood pressure measuring device comprises a mean blood pressure measuring device which measures said mean blood pressure of said subject, and said cuff pulse-wave detecting device comprises a cuff pressure holding device which holds said fluid pressure of said cuff at said reference pressure value not higher than said mean blood pressure of said subject measured by said mean blood pressure measuring device.

7. An apparatus according to claim 6, wherein said mean blood pressure measuring device comprises means for measuring said mean blood pressure of said subject while said fluid pressure of said cuff is increased to a prescribed pressure value, and said cuff pressure holding means comprises means for holding said fluid pressure of said cuff at said reference pressure value not higher than said mean blood pressure of said subject while said fluid pressure of said cuff is decreased from said prescribed pressure value.

8. An apparatus according to claim 6, wherein said mean blood pressure measuring device comprises means for determining, as said mean blood pressure of said subject, a fluid pressure of said cuff at a time of detection of a pulse having a greatest amplitude out of respective amplitudes of a plurality of pulses of a pulse wave which is produced in said cuff while said fluid pressure of said cuff is changed.

9. An apparatus according to claim 6, wherein said mean blood pressure measuring device comprises means for determining, as said mean blood pressure of said subject, a fluid pressure of said cuff at a time when a value of correlation between each pair of successive pulses of a plurality of pulses of a pulse wave which is produced in said cuff while said fluid pressure of said cuff is changed, is changed by a prescribed amount.

10. An apparatus according to claim 1, wherein said oscillometric blood pressure measuring device comprises:

a pressure pulse wave sensor which detects a radial pulse wave produced from a radial artery of said subject;

transfer function correcting means for correcting a standard transfer function from a pulse wave produced in an aorta of a standard human being to a pulse wave of said human being detected from said cuff by said cuff pulse-wave detecting device, based on said radial pulse wave of said subject detected by said pressure pulse wave sensor and said pulse wave of said subject detected from said cuff by said cuff pulse-wave detecting device; and calculating means for providing an estimated aortic pulse wave of said subject, based on said pulse wave of said subject detected from said cuff by said cuff pulse-wave detecting device, according to the corrected transfer function provided by said transfer function correcting means, wherein said waveform storing device stores, in said waveform memory, the waveform of said aortic pulse wave of said subject provided by said calculating means.

11. An apparatus according to claim 10, wherein said transfer function correcting means comprises means for correcting said standard transfer function based on a difference between said radial pulse wave of said subject and said pulse wave of said subject detected from said cuff.

* * * * *